United States Patent
Giardiello et al.

(10) Patent No.: US 9,532,979 B2
(45) Date of Patent: *Jan. 3, 2017

(54) COMPOSITIONS OF LOPINAVIR AND RITONAVIR

(75) Inventors: Marco Norman Giardiello, Liverpool (GB); Thomas Oliver McDonald, Liverpool (GB); Andrew Owen, Liverpool (GB); Steven Paul Rannard, Liverpool (GB); Philip John Martin, Liverpool (GB); Darren Lee Smith, Liverpool (GB)

(73) Assignee: The University of Liverpool, Liverpool (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/343,453

(22) PCT Filed: Sep. 7, 2012

(86) PCT No.: PCT/GB2012/052210
§ 371 (c)(1),
(2), (4) Date: Mar. 7, 2014

(87) PCT Pub. No.: WO2013/034927
PCT Pub. Date: Mar. 14, 2013

(65) Prior Publication Data
US 2014/0220141 A1    Aug. 7, 2014

(30) Foreign Application Priority Data

Sep. 9, 2011  (GB) .................... 1115635.3

(51) Int. Cl.
A61K 9/14         (2006.01)
A61K 31/427   (2006.01)
(Continued)

(52) U.S. Cl.
CPC ............... *A61K 31/427* (2013.01); *A61K 9/19* (2013.01); *A61K 9/5138* (2013.01);
(Continued)

(58) Field of Classification Search
CPC .......... A61K 31/536; A61K 9/51; A61K 9/14; A61K 9/5192; A61K 9/1682; A61K 9/5138; A61K 9/19; A61K 9/10; A61K 31/427; A61K 31/513; A61K 38/55; A61K 2300/00
(Continued)

(56) References Cited

U.S. PATENT DOCUMENTS

2010/0036000 A1*  2/2010  Lichter et al. ............. 514/772.1
2010/0143439 A1*  6/2010  Jayasuriya et al. ........... 424/423
2010/0272639 A1* 10/2010  Dutcher ...................... 424/1.37

FOREIGN PATENT DOCUMENTS

CA       2353809      6/2000
DE      19856432      6/2000
(Continued)

OTHER PUBLICATIONS

Ghosn, Jade , et al., "HIV-1 Resistance to First- and Second-Generation Non-nucleoside Reverse Transcriptase Inhibitors," AIDS Rev., 11:165-173 (2009).
(Continued)

*Primary Examiner* — Blessing M Fubara
(74) *Attorney, Agent, or Firm* — Barnes & Thornburg LLP

(57) ABSTRACT

The present inventions relates to a solid composition and an aqueous dispersion comprising nanoparticles of the antiretroviral drugs lopinavir and ritonavir. The solid composition and aqueous dispersion additionally comprise a mixture of a hydrophilic polymer and a surfactant. The surfactant is selected from vitamin-E-polyethylene glycol-succinate (Vit-
(Continued)

E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof. The hydrophilic polymer is suitably selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof. The present invention also relates to processes for preparing both the solid composition and the aqueous dispersion, as well as to their use in therapy for the treatment and/or prevention of retroviral infections such as human immunodeficiency virus (HIV).

17 Claims, 3 Drawing Sheets

(51) Int. Cl.
A61K 9/19 (2006.01)
A61K 31/513 (2006.01)
A61K 38/55 (2006.01)
A61K 9/51 (2006.01)

(52) U.S. Cl.
CPC ............ *A61K 31/513* (2013.01); *A61K 38/55* (2013.01); *A61K 9/5192* (2013.01)

(58) Field of Classification Search
USPC ........................................ 424/489; 514/230.5
See application file for complete search history.

(56) References Cited

FOREIGN PATENT DOCUMENTS

| EP | 2279728 | 2/2011 |
|---|---|---|
| WO | WO2004/011537 | 2/2004 |
| WO | WO2008/006712 | 1/2008 |
| WO | WO2008/067164 | 6/2008 |
| WO | WO2009/118356 | 10/2009 |
| WO | WO2009/153654 | 12/2009 |
| WO | WO2010/068899 | 6/2010 |
| WO | WO 2010/068899 A1 * | 6/2010 |
| WO | WO2011/128623 | 10/2011 |

OTHER PUBLICATIONS

Parikh, Nirali, et al. "Simultaneous Determination of Ketoconazole, Ritonavir and Lopinavir in Solid Lipid Nanoparticles by RP-LC," Chromatographia, 71(9-10):941-946 (May 2010).

Angshuman, B., et al., "Alginate Based Nanoparticulate Drug Delivery for Anti Hiv Drug Lopinavir," Journal of Global Pharma Technology, 2(3): 126-132 (2010).

Delaugerre, C., et al., "Protease Inhibitor Resistance Analysis in the MONARK Trial Comparing First-Line Lopinavir-Ritonavir Monotherapy to Lopinavir-Ritonavir plus Zidovudine and Lamivudine Triple Therapy," Antimicrobial Agents and Chemotherapy, 53(7): 2934-2939 (Jul. 2009).

Destache, C, et al., "Antiretroviral release from poly(DL-lactide-co-glycolide) nanoparticles in mice," J Antimicrob Chemother., 65: 2183-2187 (2010).

Owen, A., et al., "Intracellular pharmacokinetics of antiretroviral agents," J. HIV Ther., 9(4):97-101 (Nov. 2004).

PCT Search Report and Written Opinion for PCT/GB2012/052210, completed Jan. 2, 2013.

United Kingdom Search Report and Written Opinion for 1115635.3, completed Jan. 4, 2012.

* cited by examiner

COMPOSITIONS OF LOPINAVIR AND RITONAVIR

CROSS-REFERENCE TO RELATED APPLICATIONS

This application is a national stage entry under 35 USC §371(b) of PCT International Application No. PCT/GB2012/052210, filed Sep. 7, 2012, which claims priority to United Kingdom Patent Application No. 1115635.3, filed Sep. 9, 2011, the entire disclosures of all of which are incorporated herein by reference.

INTRODUCTION

The present invention relates to compositions of the anti-HIV drug combination lopinavir and ritonavir that are suitable for pharmaceutical use. More specifically, the present invention relates to a solid composition of lopinavir and ritonavir and, in another aspect, to an aqueous dispersion of lopinavir and ritonavir. The present invention also relates to processes for preparing both the solid composition and the aqueous dispersion, as well as to their use in therapy for the treatment and/or prevention of retroviral infections such as human immunodeficiency virus (HIV).

BACKGROUND OF THE INVENTION

Human Immunodeficiency Virus (HIV) is a major cause of morbidity and mortality in both the developed and the developing world. HIV is a retrovirus that causes acquired immunodeficiency syndrome (AIDS) in humans, which in turn allows life-threatening infections and cancers to thrive as the immune system progressively fails.

HIV infection typically occurs through the transfer of bodily fluids, such as blood, semen, vaginal fluid, pre-ejaculate, or breast milk, from one individual to another. HIV may be present within these bodily fluids as either the free virus, or as a virus present within the infected immune cells. HIV-1 tends to be the most virulent form of HIV, and is transmitted as a single-stranded enveloped RNA virus which, upon entry into a target cell, is converted into double-stranded DNA by reverse transcription. This DNA may then become integrated into the host's DNA where it can reside in a latent from and avoid detection by the immune system. Alternatively, this DNA may be re-transcribed into RNA genomes and translated to form viral proteins that are released from cells as new virus particles, which can then spread further.

Treatments of HIV, particularly HIV-1, commonly involve combination therapy with a co-formulation of lopinavir (LPV) and ritonavir (RTV). Such co-formulations are currently sold commercially as either film coated tablets or an oral solution both under the trade name Kaletra®. Lopinavir and Ritonavir are both protease inhibitors (PI) widely used in antiretroviral therapy. However, Ritonavir is no longer commonly used for its own antiretroviral activity but rather to boost the activity of other protease inhibitors, such as Lopinavir. In particular, Ritonavir is used to inhibit liver enzymes (e.g. cytochrome P450-3A4-CYP3A4) responsible for metabolising protease inhibitors such as lopinavir. Such metabolism inhibition allows for higher blood plasma concentrations of protease inhibitors such as Lopinavir, thereby allowing lower doses of Lopinavir to be administered. This in turn reduces the adverse side effects associated with high doses of Lopinavir.

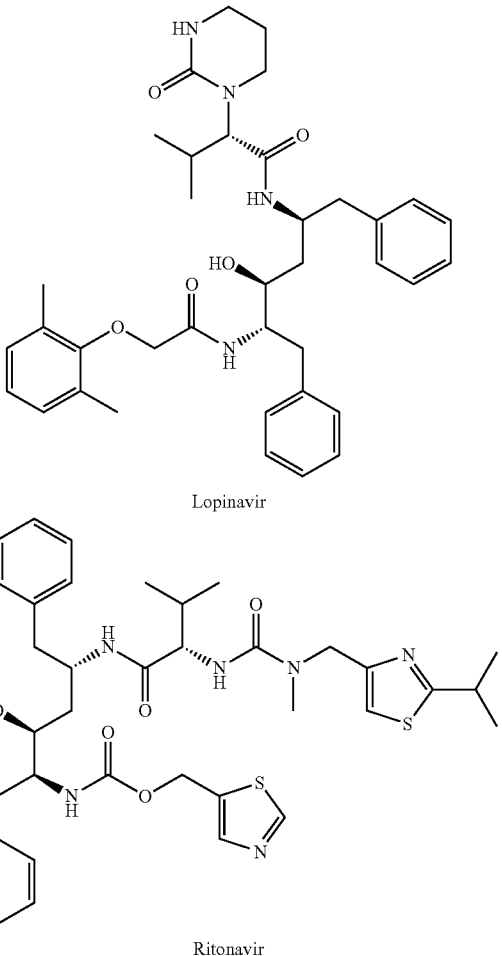

Lopinavir

Ritonavir

Although current co-formulations of lopinavir and ritonavir are effective in prolonging life expectancy in HIV suffers, there remain a number of drawbacks associated with the currently available formulations.

Lopinavir acts on an intracellular target, so the ability of lopinavir to penetrate and accumulate within cells is a prerequisite for effective treatment (Owen and Khoo, *Journal of HIV Therapy*, 2004, 9(4), 53-57). One particular problem with the current formulations of lopinavir and ritonavir is that the penetration of lopinavir into cells is variable and inadequate both within and between patients. As cellular penetration and accumulation of the drug is necessary in order to effectively treat the HIV infected cells, there is a need for combination formulations of lopinavir and ritonavir that exhibit good levels of cellular accumulation, particularly in immune cells (e.g. macrophages and CD4+ lymphocytes).

In addition, the distribution of lopinavir throughout the body is also not uniform with current LPV/RTV co-formulations, and certain target tissues and sanctuary sites, such as the brain and the testis, suffer from poor exposure to the lopinavir. This can lead to sub-therapeutic levels of the drug reaching certain tissues, with the consequential effect that HIV infected cells residing in these tissues may not be adequately treated. Furthermore, resistance to lopinavir is becoming an increasing problem (Goshn et al., *AIDS*, 2009, 11, 165-173) and exposure to sub-therapeutic levels of lopinavir in these tissues increases the risk that lopinavir-resistant strains of HIV can arise and reseed the blood. Resistant strains of HIV are also transmittable meaning that individuals can be newly infected with resistant virus. There is, therefore, a need for LPV/RTV formulations that provide an improved distribution of lopinavir throughout the body, and in particular to sanctuary sites for the virus.

A further problem with current LPV/RTV co-formulations is that it is necessary to administer large doses of lopinavir each day (typically the adult dose is 400 mg/100 mg lopinavir/ritonavir twice daily), despite the "boost" effect provided by ritonavir. As a consequence, a patient will need to consume a large tablet or capsule of LPV/RTV or multiple smaller dosage tablets or capsules in order to obtain the required dosage. This can inevitably lead to problems with patient compliance. Furthermore, lopinavir treatment is also associated with a number of adverse side effects, which represent a major problem for patients, especially over prolonged periods (Delaugerre et al., *Antimicrob. Agents Chemother.*, 2009, 53(7), 2934-2939). For these reasons, there is a need for more effective formulations of LPV/RTV, which in turn may enable the required dosage of lopinavir to be reduced. Lower doses could have an effect on the number and/or size of the tablets/capsules that need to be consumed by the patient, as well as prevalence of the adverse side effects.

A further problem with current LPV/RTV co-formulations is that the ratio of lopinavir/ritonavir is relatively low (typically 4:1) and thus doses of ritonavir are high. Ritonavir itself gives rise to adverse side effects and, in addition, detrimentally affects the efficacy of many other medications. This can lead to difficulties when certain other drugs are co-administered with ritonavir.

There is also a need for dosage forms that permit the dosage to be easily varied on a patient-by-patient basis depending on factors such as the age (including paediatric dosing) and weight of the patient, as well as the severity and stage of the infection.

It is therefore an object of the present invention to provide improved LPV/RTV co-formulations that address one or more of the drawbacks associated with the current LPV/RTV co-formulations.

In particular, it is an object of the invention is to provide a LPV/RTV co-formulations exhibiting good cell penetration and a more optimum and effective distribution throughout the body.

Another object of the present invention is to provide a LPV/RTV co-formulation with a high drug loading.

Another object of the present invention is to provide a formulation which permits lower overall dosage levels of either or both of lopinavir and ritonavir in HIV treatments.

SUMMARY OF THE INVENTION

According to a first aspect of the present invention there is provided a solid composition, comprising nanoparticles of lopinavir and ritonavir dispersed within a mixture of at least one hydrophilic polymer and at least one surfactant;

wherein the hydrophilic polymer is selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof; and wherein the surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof.

According to a second aspect of the present invention there is provided an aqueous dispersion, comprising a plurality of nanoparticles of lopinavir and ritonavir dispersed in an aqueous medium, the nanoparticles comprising a core of lopinavir and/or ritonavir and a coating of at least one hydrophilic polymer and at least one surfactant;

wherein the hydrophilic polymer is selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof; and wherein the surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof.

Both the solid composition and the aqueous dispersion of the present invention comprise the lopinavir and ritonavir drug substances in nanoparticulate form. The nanoparticles of the present invention provide improved dosage forms of lopinavir/ritonavir, particularly with respect to stability and efficacy. The solid composition and the aqueous dispersion of the present invention also provide good cell penetration and accumulation, especially in immune cells. In certain embodiments, the level of cell penetration is significantly improved relative to conventional formulations. The solid composition and the aqueous dispersion of the present invention also provide an improved distribution of drugs throughout the body and provide higher drug levels in certain target tissues such as the testes and brain. These advantages provide the opportunity for a more effective treatment of HIV and may also enable the required dosage of lopinavir and ritonavir to be reduced.

The nanoparticles of lopinavir and ritonavir also possess low cytotoxicity, and compositions with high drug loadings can be prepared.

The provision of nanoparticles in a solid composition can also be advantageous because it provides a more stable form of the drug that is suitable for long term storage. Furthermore, the solid composition can be consumed as a solid dosage form when required in certain embodiments of the invention, or, alternatively, they can be dispersed in a suitable aqueous diluent when required to form an aqueous dispersion of the nanoparticles for administration.

Furthermore, the solid compositions of the present invention allow for higher drug loadings than known lopinavir and ritonavir formulations, which enables excipient dosages (e.g. surfactants) and the overall size of the dosage form to be reduced.

The solid compositions of the present invention are ideally suited to personalised medicine regimes, because the solid compositions are substantially homogeneous, meaning that partial doses may be accurately measured. Furthermore, the solid compositions of the present invention are readily dispersible within an aqueous medium to provide stable aqueous dispersions. Such stable aqueous dispersions can themselves be partitioned in a pre-determined manner to provide an accurate liquid dose of lopinavir and ritonavir. Such methods of providing personalised doses are particularly applicable to paediatric administration, since children require lower doses of lopinavir and ritonavir. Moreover, lopinavir and ritonavir doses can be accordingly adapted to suit a patient's weight, age, and other circumstances (such as the stage or severity of the HIV infection).

Finally, in particular embodiments of the invention, each nanoparticle comprises both LPV and RTV in a fixed ratio. This can provide formulation advantages because only one material comprising both drugs needs to be handled and formulated. For example, only one material needs to be used for the preparation of a tablet or capsule formulation. Furthermore, only one material comprising both drugs is needed to prepare the aqueous dispersion formulations defined herein.

According to a third aspect of the present invention there is provided a solid composition, comprising nanoparticles of ritonavir dispersed within a mixture of at least one hydrophilic polymer and at least one surfactant;

wherein the hydrophilic polymer is selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof; and wherein the surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof.

According to a fourth aspect of the present invention there is provided an aqueous dispersion, comprising a plurality of nanoparticles of ritonavir dispersed in an aqueous medium, the nanoparticles comprising a core of ritonavir and a coating of at least one hydrophilic polymer and at least one surfactant;

wherein the hydrophilic polymer is selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof; and wherein the surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof.

According to a fifth aspect of the invention, there is provided an aqueous dispersion, obtainable by, obtained by, or directly obtained by dispersing the solid composition of the first or third aspects in an aqueous medium.

According to a sixth aspect of the present invention there are provided processes for the preparation of a solid composition as defined herein.

According to a seventh aspect of the present invention, there is provided a solid composition obtainable by, obtained by, or directly obtained by any of the processes according to the sixth aspect.

According to an eighth aspect of the present invention, there is provided a pharmaceutical composition comprising a solid composition of the first, third or seventh aspects of the invention, or an aqueous dispersion of the second, fourth or fifth aspects of the invention, and optionally a further pharmaceutically acceptable diluent, carrier, or excipient.

According to a ninth aspect of the present invention, there is provided a solid composition or an aqueous dispersion as defined herein for use as a medicament.

According to a tenth aspect of the present invention, there is provided a solid composition or an aqueous dispersion as defined herein for use in the treatment and/or prevention of retroviral infections (e.g. HIV).

According to a eleventh aspect of the present invention, there is provided a use of a solid composition or an aqueous dispersion as defined herein in the manufacture of a medicament for use in the treatment and/or prevention of retroviral infections (e.g. HIV).

According to a twelfth aspect of the present invention, there is provided a method of treating and/or preventing a retroviral infection (e.g. HIV), comprising administering a therapeutically effective amount of a solid composition, an aqueous dispersion, or a pharmaceutical composition as defined herein to a patient suffering from or at risk of suffering from the retroviral infection.

According to an thirteenth aspect of the present invention there is provided a kit of parts comprising a solid composition as defined herein or pharmaceutical composition comprising the solid composition as defined herein, and a pharmaceutically acceptable diluent.

Features, including optional, suitable and preferred features of any aspect of the invention are, unless otherwise stated, also features, including optional, suitable and preferred features of any other aspect of the invention.

BRIEF DESCRIPTION OF THE FIGURES

In the Example section reference is made to the following figures.

DETAILED DESCRIPTION OF THE INVENTION

Definitions

Figure 1:
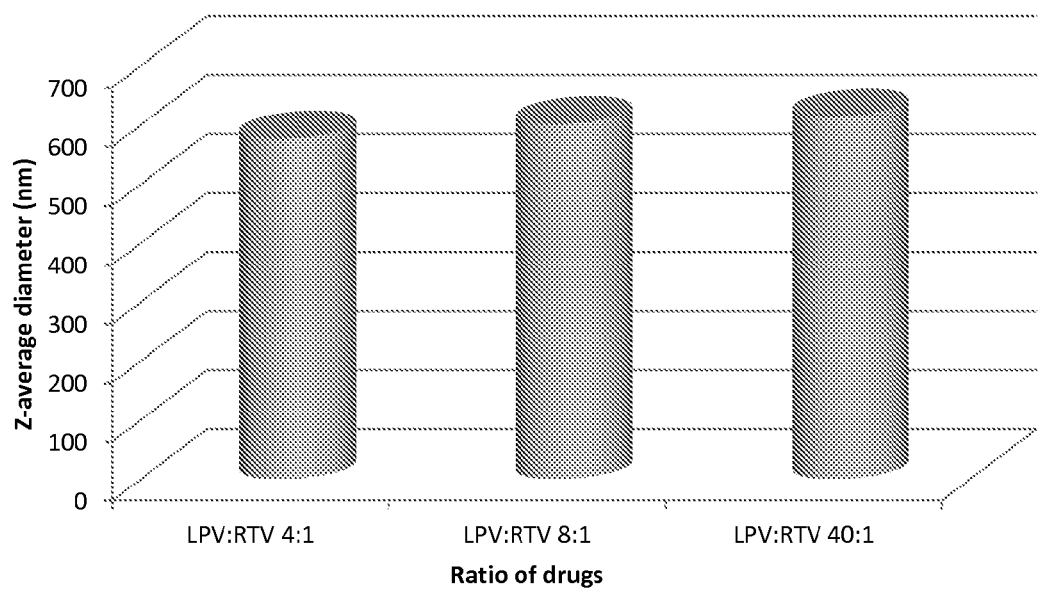
FIG. 1 shows a 3-D bar chart displaying the z-average particle size for the three lopinavir and ritonavir combination ratios prepared in Example 1.

The term "nanoparticle" or "nanoparticulate" is used herein to mean a particle having a size of less than or equal to 1 micron (μm).

The term "lopinavir" is used herein to refer to lopinavir, which is commonly used in HIV treatment, and includes pharmaceutically acceptable salts and solvates thereof, as well as any polymorphic or amorphous forms thereof.

The term "ritonavir" is used herein to refer to ritonavir, which is commonly used in HIV treatment, and includes pharmaceutically acceptable salts and solvates thereof, as well as any polymorphic or amorphous forms thereof.

It is to be appreciated that references to "preventing" or "prevention" relate to prophylactic treatment and includes preventing or delaying the appearance of clinical symptoms of the state, disorder or condition developing in a human that may be afflicted with or predisposed to the state, disorder or condition but does not yet experience or display clinical or subclinical symptoms of the state, disorder or condition.

It will be appreciated that references to "treatment" or "treating" of a state, disorder or condition includes: (1) inhibiting the state, disorder or condition, i.e., arresting, reducing or delaying the development of the disease or a relapse thereof (in case of maintenance treatment) or at least one clinical or subclinical symptom thereof, or (2) relieving or attenuating the disease, i.e. causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the patient to be treated.

The term "consisting essentially of" is used herein to denote that a given component is primarily composed of a designated material. Suitably, such a component comprises greater than or equal to 85% of the designated material, more suitably greater than or equal to 90%, more suitably greater than or equal to 95%, most suitably greater than or equal to 98% of the designated material. By way of example, an individual nanoparticle consisting essentially of lopinavir is a nanoparticle primarily composed of lopinavir.

Solid Lopinavir/Ritonavir Composition

The present invention provides a solid lopinavir/ritonavir (LPV/RTV) composition, comprising nanoparticles of lopinavir and ritonavir dispersed within a mixture of at least one hydrophilic polymer and at least one surfactant;

wherein the hydrophilic polymer is selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof; and wherein the surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof.

The nanoparticles of lopinavir and ritonavir drug substances are dispersed within a solid excipient mixture comprising the hydrophilic polymer and the surfactant. The nanoparticles of lopinavir and ritonavir collectively comprise a mixture of lopinavir and ritonavir, though individual nanoparticles may comprise both lopinavir and ritonavir, may consist essentially of lopinavir, or may consist essentially of ritonavir.

In a particular embodiment, the nanoparticles of lopinavir and ritonavir comprise individual nanoparticles comprising both lopinavir and ritonavir. In a particular embodiment, the nanoparticles of lopinavir and ritonavir consist essentially of individual nanoparticles comprising both lopinavir and ritonavir.

In another embodiment, the nanoparticles of lopinavir and ritonavir comprise individual nanoparticles comprising lopinavir, and individual nanoparticles comprising ritonavir.

In a particular embodiment, the nanoparticles of lopinavir and ritonavir comprise a mixture of individual nanoparticles comprising both lopinavir and ritonavir, individual nanoparticles consisting essentially of lopinavir, and/or individual nanoparticles consisting essentially of ritonavir. The solid composition of the present invention may be administered as it is to a patient, or further formulated to provide a pharmaceutical composition in the form of, for example, a tablet, capsule, lozenge, or a dispersible powder or granule formulation.

The nanoparticles of lopinavir and ritonavir have an average particle size of less than or equal to 1 micron ($\mu$m). In a particular embodiment, the nanoparticles of lopinavir and ritonavir have an average particle size of between 100 and 1000 nm. In another embodiment, the nanoparticles of lopinavir and ritonavir have an average particle size between 400 and 850 nm.

The particle size of the nanoparticles may be assessed by any suitable technique known in the art (e.g. laser diffraction, laser scattering, electron microscopy). In an embodiment of the invention, particle size is assessed by dispersing the solid composition in an aqueous medium and determining the particle size with a Zetasizer (Malvern Instruments Ltd).

In an embodiment, the polydispersity of the nanoparticles of lopinavir and ritonavir is less than or equal to 0.8, suitably less than or equal to 0.6, and most suitably less than or equal to 0.5. The polydispersity relates to the size of the lopinavir and ritonavir nanoparticles and may be determined by suitable techniques known in the art (e.g. laser diffraction, laser scattering, electron microscopy). In an embodiment of the present invention, the polydispersity of particle sizes of the nanoparticles of lopinavir and ritonavir may be suitably assessed with a Malvern Zetasizer (Malvern Instruments Ltd).

In a particular embodiment, the average zeta potential of the nanoparticles of lopinavir and ritonavir when dispersed in an aqueous medium is between −100 and +100 mV. In another embodiment, the zeta potential of the nanoparticles of lopinavir and ritonavir is between −25 and +25 mV. In another embodiment, the zeta potential of the nanoparticles of lopinavir and ritonavir is between −20 and +20 mV. In yet another embodiment, the zeta potential of the nanoparticles of lopinavir and ritonavir is between −25 and 0 mV. In general it has been found that zeta potentials of a relatively small magnitude (either positive or negative) allow the nanoparticles to better penetrate into and accumulate within cells. In accordance with the present invention, average zeta potentials can be measured by techniques known in the art, such as using a Zetasizer (Malvern Instruments Ltd).

The solid composition may comprise particles or granules of larger size, for example, 5 to 30 microns ($\mu$m) in size, but each particle or granule contain a plurality of nanoparticles of lopinavir and ritonavir dispersed within a mixture of the hydrophilic polymer and surfactant. Furthermore, these larger particles or granules disperse when the solid composition is mixed with an aqueous medium to form discrete nanoparticles of lopinavir and ritonavir.

In an embodiment, the solid composition comprises a single hydrophilic polymer and a single surfactant selected from those listed herein. In an alternative embodiment, the solid composition comprises two or more hydrophilic polymers and/or two or more surfactant selected from those listed herein may be present.

Hydrophilic Polymer

A wide range of hydrophilic polymers are suitable for use in pharmaceutical formulations. Examples of such polymers include:

(a) homo or co-polymers of monomers selected from: vinyl alcohol, acrylic acid, methacrylic acid, acrylamide, methacrylamide, acrylamide aminoalkylacrylates, aminoalkylmethacrylates, hydroxyethylacrylate, methylpropane sulphonates, hydroxyethylmethylacrylate, vinyl pyrrolidone, vinyl imidazole, vinyl amines, vinyl pyridine, ethyleneglycol, propylene glycol, ethylene oxides, propylene oxides, ethyleneimine, styrenesulphonates, ethyleneglycolacrylates and ethyleneglycol methacrylate;

(b) polyvinyl alcohol (PVA), a polyvinyl alcohol-polyethylene glycol graft copolymer, a block copolymer of polyoxyethylene and polyoxypropylene, polyethylene glycol, and polyvinylpyrrolidone, or a combination thereof (c) cellulose derivatives for example cellulose acetate, methylcellulose, methyl-ethylcellulose, hydroxy-ethylcellulose, hydroxy-ethylmethyl-cellulose, hydroxy-propylcellulose (HPC), hydroxy-propylmethylcellulose (HPMC), hydroxypropylbutylcellulose, ethylhydroxy-ethylcellulose, carboxymethylcellulose and its salts (eg the sodium salt—SCMC), or carboxy-methylhydroxyethylcellulose and its salts (for example the sodium salt)

(d) gums such as guar gum, alginate, locust bean gum and xanthan gum (e) polysaccharides such as dextran, xyloglucan and gelatin (or hydrolysed gelatin);

(f) cyclodextrins such as beta-cyclodextrin;

(g) mixtures thereof.

Copolymers may be statistical copolymers (also known as a random copolymer), a block copolymer, a graft copolymer or a hyperbranched copolymer. Additional co-monomers may also be present provided that their presence does not effect the water-solubility of the resulting polymeric material.

Particular examples of homopolymers include poly-vinyl-alcohol (PVA), poly-acrylic acid, poly-methacrylic acid, poly-acrylamides (such as poly-N-isopropylacrylamide), poly-methacrylamide; poly-acrylamines, poly-methyl-acrylamines, (such as polydimethylaminoethylmethacrylate and poly-N-morpholinoethylmethacrylate), polyvinylpyrrolidone (PVP), poly-styrenesulphonate, polyvinylimidazole, polyvinylpyridine, poly-2-ethyl-oxazoline poly-ethyleneimine and ethoxylated derivatives thereof.

In the present invention, the hydrophilic polymer is selected from those hydrophilic polymers that are capable of stabilising nanoparticles of lopinavir and ritonavir in an aqueous dispersion together with a surfactant as defined herein, and which are also suitable for pharmaceutical use (e.g. they are approved for use by the US Food and Drug Administration).

The hydrophilic polymer is therefore suitably selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof.

It shall be appreciated that any molecular weight (Mw) or molecular number (Mn) values quoted herein span the range of Mw and Mn values that may be present in the polymer.

In a particular embodiment, the polyvinyl alcohol has an average molecular weight between 5000 and 200000 Da, suitably with a 75-90% hydrolysis level (i.e. % free hydroxyls). In a particular embodiment, the polyvinyl alcohol has a 75-90% hydrolysis level. In another embodiment, the polyvinyl alcohol has a 75-85% hydrolysis level. In a particular embodiment, the polyvinyl alcohol has an average molecular weight between 9000 and 10000 Da, suitably with an 80% hydrolysis level.

In a particular embodiment, the polyvinyl alcohol-polyethylene glycol graft copolymer has an average molecular weight between 30000 and 60000 Da, suitably with a PVA/PEG ratio of between 90:10 and 25:75. In a particular embodiment, the polyvinyl alcohol-polyethylene glycol graft copolymer has an average molecular weight between 40000 and 50000 Da, suitably with a PVA/PEG ratio of between 85:15 and 25:75. Suitably the polyvinyl alcohol-polyethylene glycol graft copolymer has a PVA/PEG ratio of between 90:10 and 25:75, more suitably a PVA/PEG ratio of between 85:15 and 25:75. In a particular embodiment, the polyvinyl alcohol-polyethylene glycol graft copolymer is a Kollicoat® polymer (supplied by BASF). In a particular embodiment, the Kollicoat® is Kollicoat® Protect.

The block copolymer of polyoxyethylene and polyoxypropylene is suitably either a diblock copolymer of polyoxyethylene and polyoxypropylene or a triblock copolymer thereof. In a particular embodiment, the block copolymer of polyoxyethylene and polyoxypropylene is a Poloxamer.

A "poloxamer" is a non-ionic triblock copolymer comprising a central hydrophobic chain of polyoxypropylene, and hydrophilic chains of polyoxyethylene either side of this central hydrophobic chain. A "poloxamer" is typically named with the letter "P" followed by three numerical digits (e.g. P407), where the first two digits multiplied by 100 gives the approximate molecular mass of the polyoxypropylene chain, and the third digit multiplied by 10 provides the percentage polyoxyethylene content of the poloxamer. For example, P407 is a poloxamer having a polyoxypropylene molecular mass of about 4,000 g/mol and a polyoxyethylene content of about 70%. Poloxamers are also known as Pluronics®, as well as by several other commercial names.

The Poloxamer is suitably a pharmaceutically acceptable Poloxamer. In a particular embodiment, the poloxamer is Poloxamer P407 or Poloxamer P188.

In a particular embodiment, the polyethylene glycol (PEG) has an average molecular weight of 500 to 20000 Da. In a particular embodiment, the polyethylene glycol is PEG 1K (i.e. with an average molecular weight of about 1000 Da).

In a particular embodiment, the HPMC has an average molecular weight of 10000 to 400000 Da. In a particular embodiment, the HPMC has an average molecular weight of about 10000.

In a particular embodiment, the polyvinylpyrrolidone has an average molecular weight of 2000 to 1,000,000 Da. In a particular embodiment, the polyvinylpyrrolidone has an average molecular weight of 30000 to 55000 Da. In a particular embodiment, the polyvinylpyrrolidone is polyvinylpyrrolidone K30 (PVP K30).

In a particular embodiment, the hydrophilic polymer is selected from PVA, a Kollicoat®, Poloxamer 407, PEG 1K, HPMC, PVP K30, and Poloxamer 188, or a combination thereof.

In a particular embodiment, the hydrophilic polymer is PVA.

Surfactant

Surfactants suitable for pharmaceutical use may be:
non-ionic (e.g. ethoxylated triglycerides; fatty alcohol ethoxylates; alkylphenol ethoxylates; fatty acid ethoxylates; fatty amide ethoxylates; fatty amine ethoxylates; sorbitan alkanoates; ethylated sorbitan alkanoates;

alkyl ethoxylates; Pluronics™; alkyl polyglucosides; stearol ethoxylates; alkyl polyglycosides; sucrose fatty acid esters, anionic, cationic, amphoteric or zwitterionic);

anionic (e.g. alkylether sulfates; alkylether carboxylates; alkylbenzene sulfonates; alkylether phosphates; dialkyl sulfosuccinates; sarcosinates; alkyl sulfonates; soaps; alkyl sulfates; alkyl carboxylates; alkyl phosphates; paraffin sulfonates; secondary n-alkane sulfonates; alpha-olefin sulfonates; isethionate sulfonates; alginates);

cationic (e.g. fatty amine salts; fatty diamine salts; quaternary ammonium compounds; phosphonium surfactants; sulfonium surfactants; sulfonxonium surfactants); or zwitterionic (e.g. N-alkyl derivatives of amino acids (such as glycine, betaine, aminopropionic acid); imidazoline surfactants; amine oxides; amidobetaines).

Alkoxylated nonionic's (especially the PEG/PPG Pluronic™ materials), phenol-ethoxylates (especially TRITON™ materials), alkyl sulphonates (especially SDS), ester surfactants (preferably sorbitan esters of the Span™ and Tween™ types) and cationics (especially cetyltrimethylammonium bromide—CTAB) are particularly suitable as surfactants.

In the present invention, the surfactant is suitably selected from those surfactants that are capable of stabilising nanoparticles of lopinavir and ritonavir together with a hydrophilic polymer as defined herein, and which are also approved for pharmaceutical use (e.g. they are approved for use by the US Food and Drug Administration).

The surfactant is therefore suitably selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof.

It will be appreciated that the hydrophilic polymer and the surfactant may both be either PVA or a block copolymer of polyoxyethylene and polyoxypropylene. In other words, the PVA and block copolymer of polyoxyethylene and polyoxypropylene may function as both the surfactant and the hydrophilic polymer. The total amount of PVA or block copolymer of polyoxyethylene and polyoxypropylene that may be present in such circumstances is that defined hereinafter for the total of the surfactant and hydrophilic polymer.

In a particular embodiment, the surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, and polyethyleneglycol-12-hydroxystearate, or a combination thereof.

In a particular embodiment, the vitamin-E-polyethylene glycol-succinate (Vit-E-PEG-succinate) has a PEG moiety with an average molecular weight of 500 to 10000 Da. In a particular embodiment, the vitamin-E-polyethylene glycol-succinate (Vit-E-PEG-succinate) has a PEG portion with an average molecular weight of about 1000 Da (which is commercially available as Tocofersolan).

In a particular embodiment, the polyoxyethylene sorbitan fatty acid ester is selected from Polysorbate 20 (commercially available as Tween® 20) and Polysorbate 80 (commercially available as Tween® 80).

In a particular embodiment, the polyethyleneglycol-12-hydroxystearate has a molecular weight of 300 to 3000 Da. In a particular embodiment, the polyethylenglycol-12-hydroxystearate has a molecular weight of 600 to 700 Da (e.g. commercially available as Solutol® HS).

In a particular embodiment, the surfactant is selected from vitamin-E-polyethylene glycol-succinate (Vit-E-PEG-succinate), Polysorbate 20, Polysorbate 80, N-alkyldimethylbenzylammonium chloride (e.g. commercially available as Hyamine®), sodium deoxycholate, dioctyl sodium sulfosuccinate (e.g. AOT), and polyethyleneglycol-12-hydroxystearate (e.g. Solutol® HS), or a combination thereof.

In an embodiment, the surfactant is selected from vitamin-E-polyethylene glycol-succinate (Vit-E-PEG-succinate), Polysorbate 20, Polysorbate 80, and sodium deoxycholate.

In a particular embodiment, the surfactant is selected from vitamin-E-polyethylene glycol-succinate (Vit-E-PEG-succinate), Polysorbate 20, and Polysorbate 80.

In a particular embodiment, the surfactant is selected from vitamin-E-polyethylene glycol-succinate (Vit-E-PEG-succinate), and Polysorbate 80.

In a particular embodiment, the surfactant is vitamin-E-polyethylene glycol-succinate (Vit-E-PEG-succinate).

Particular Combinations of Hydrophilic Polymer and Surfactant

PVA is a particularly suitable hydrophilic polymer where the surfactant is selected from vitamin-E-polyethylene glycol-succinate (Vit-E-PEG-succinate), Polysorbate 20, Polysorbate 80, and sodium deoxycholate.

PVA is a particularly suitable hydrophilic polymer where the surfactant is selected from vitamin-E-polyethylene glycol-succinate (Vit-E-PEG-succinate), Polysorbate 20, and Polysorbate 80.

PVA is a particularly suitable hydrophilic polymer where the surfactant is selected from vitamin-E-polyethylene glycol-succinate (Vit-E-PEG-succinate), and Polysorbate 80.

PVA is a particularly suitable hydrophilic polymer where the surfactant is vitamin-E-polyethylene glycol-succinate.

Formulation of the Solid Composition

In a particular embodiment, the solid composition as defined herein comprises 40 to 90 wt % of lopinavir and ritonavir combined. In another embodiment, the solid composition comprises 50 to 75 wt % of lopinavir and ritonavir combined. In another embodiment, the solid composition comprises 60 to 70 wt % of lopinavir and ritonavir combined.

The solid compositions of the present invention therefore permit high drug loadings, which keeps the potentially toxic excipients (e.g. surfactants) to a minimum.

Lopinavir and ritonavir are suitably present within the solid composition in a respective ratio (LPV/RTV) between 30:1 and 1:10, more suitably between 20:1 and 1:1, most suitably between 10:1 and 2:1. In a particular embodiment, the ratio of lopinavir to ritonavir is about 8:1. In another embodiment, the ratio of lopinavir to ritonavir is about 4:1.

Suitably, the solid composition comprises 10 to 60 wt % of the hydrophilic polymer and surfactant combined, more suitably 20 to 60 wt %, even more suitably 25 to 50 wt %, most suitably 25 to 40 wt %. In a particular embodiment, the solid composition comprises 25 to 35 wt % of the hydrophilic polymer and surfactant combined.

In a particular embodiment, the solid composition comprises 5 to 50 wt % of hydrophilic polymer. In another embodiment, the solid composition comprises 10 to 40 wt % of hydrophilic polymer. In another embodiment, the solid composition comprises 15 to 30 wt % of hydrophilic polymer. In a particular embodiment, the solid composition comprises 15 to 25 wt % of hydrophilic polymer.

In a particular embodiment, the solid composition comprises 1 to 25 wt % of surfactant. In another embodiment, the solid composition comprises 2 to 20 wt % of surfactant. In another embodiment, the solid composition comprises 3 to 10 wt % of surfactant.

Where either PVA or the block copolymer of polyoxyethylene and polyoxypropylene serve both as the surfactant and the hydrophilic polymer, the abovementioned wt % values for the hydrophilic polymer and surfactant combined still apply. For example, where either PVA or the block copolymer of polyoxyethylene and polyoxypropylene serve both as the surfactant and the hydrophilic polymer, the solid composition suitably comprises 10 to 60 wt % of PVA or a block copolymer of polyoxyethylene and polyoxypropylene; more suitably 20 to 60 wt % of PVA or a block copolymer of polyoxyethylene and polyoxypropylene, even more suitably 25 to 50 wt % of PVA or a block copolymer of polyoxyethylene and polyoxypropylene, most suitably 25 to 40 wt % of PVA or a block copolymer of polyoxyethylene and polyoxypropylene. In a particular embodiment, the solid composition comprises 25 to 35 wt % of PVA or a block copolymer of polyoxyethylene and polyoxypropylene.

In an embodiment, the solid composition comprises the hydrophilic polymer and surfactant in a respective ratio of between 30:1 and 1:10. In a particular embodiment, the solid composition comprises the hydrophilic polymer and surfactant in a respective ratio of between 15:1 and 1:2. In another embodiment, the solid composition comprises the hydrophilic polymer and surfactant in a respective ratio of between 10:1 and 2:1. In a particular embodiment, the solid composition comprises the hydrophilic polymer and surfactant in a respective ratio of between 6:1 and 3:1.

In a particular embodiment, the solid composition comprises:
  40 to 80 wt % lopinavir and ritonavir combined;
  10 to 40 wt % hydrophilic polymer; and
  2 to 20 wt % surfactant.

In a particular embodiment, the solid composition comprises 15-25 wt % PVA as the hydrophilic polymer, and 5-15 wt % vitamin-E-polyethylene glycol-succinate (Vit-E-PEG-succinate) as the surfactant. In a particular embodiment, the solid composition comprises 20-25 wt % PVA as the hydrophilic polymer, and 5-10 wt % vitamin-E-polyethylene glycol-succinate (Vit-E-PEG-succinate) as the surfactant. In a particularly preferred embodiment, the solid composition comprises 18-22 wt % PVA as the hydrophilic polymer, and 8-12 wt % vitamin-E-polyethylene glycol-succinate (Vit-E-PEG-succinate) as the surfactant. Suitably, such compositions comprise 25 to 35 wt % of the hydrophilic polymer and surfactant combined, more suitably 28 to 32 wt %. In such embodiments, the solid composition suitably comprises nanoparticles having an average particle size between 500 and 650 nm, and an average zeta potential when dispersed in an aqueous medium between 0 mV and −25 mV.

Unless otherwise stated, the above weight percentages relate to the % by weight of a particular constituent as a proportion of the total weight of the solid composition.

The solid composition may comprise one or more additional excipients, for instance, to further facilitate dispersion or stabilisation of dispersions of the nanoparticles either in a pharmaceutically acceptable diluent or in vivo.

Processes for Preparing the Solid Composition

Solid compositions of the present invention may be prepared by a number of methods well known in the art. Suitable techniques for forming such compositions are described in general terms in Horn and Reiger, *Angew. Chem. Int. Ed.,* 2001, 40, 4330-4361.

For example, the solid composition may be prepared by milling a solid form of lopinavir and ritonavir. The milling may occur in the presence of the hydrophilic polymer and surfactant, or, alternatively, they may be mixed with the milled drugs after the milling step.

However, it is generally preferred that the solid lopinavir and ritonavir compositions of the present invention are prepared by an oil in water emulsion technique whereby the lopinavir and ritonavir are dissolved in the oil phase and the hydrophilic polymer and surfactant are present in the water phase. The oil and water solvents are then removed by freeze drying, spray drying or spray granulation to provide a solid composition according to the invention.

As previously highlighted, in some embodiments the solid composition comprises individual nanoparticles comprising both lopinavir and ritonavir, in which case both lopinavir and ritonavir must be present during to nanoparticle formation. In alternative embodiments, the solid composition comprises individual nanoparticles of lopinavir and individual nanoparticles of ritonavir, in which case each set of individual nanoparticles are formed separately before being subsequently mixed or blended. A mixture of these two processes is also feasible.

Thus, in accordance with one aspect of the present invention, there is provided a process for preparing a solid composition as defined herein, the process comprising:
  (a) preparing an oil in water emulsion comprising:
    an oil phase comprising both lopinavir and ritonavir; and
    an aqueous phase comprising a hydrophilic polymer and a surfactant, each as defined herein; and
  (b) removing the oil and water from the oil in water emulsion to form the solid composition.

In accordance with another aspect of the present invention, there is provided a process for preparing a solid composition as defined herein, the process comprising:
  (a) preparing an LPV oil in water emulsion comprising:
    an oil phase comprising lopinavir; and
    an aqueous phase comprising a hydrophilic polymer and a surfactant, each as defined herein;
  (b) preparing an RTV oil in water emulsion comprising:
    an oil phase comprising ritonavir; and
    an aqueous phase comprising a hydrophilic polymer and a surfactant, each as defined herein;
  (c) removing the oil and water from the LPV oil in water emulsion to form an LPV solid product;
  (d) removing the oil and water from the RTV oil in water emulsion to produce an RTV solid product;
  (e) blending together the LPV and RTV solid products to form the solid composition.

An advantage of the processes of the present invention is that the emulsions formed in the initial steps are sufficiently homogenous and stable to allow for effective and uniform drying upon removal of the oil and water. Furthermore, the nanoparticles formed are substantially uniform in their physical form (size, shape etc.).

The oil in water formation steps may be performed by methods well-known in the art. Any suitable method for forming the oil in water emulsions may therefore be used. In particular, mixing of the oil and water phases to form the oil in water emulsion may be performed by methods well known in the art. For example, the mixing may involve stirring, sonication, homogenisation, or a combination thereof. In a particular embodiment, the mixing is facilitated by sonication and/or homogenisation.

The oil in water formation steps may be performed, for example, by using the methods described in WO 2004/011537 A1 (COOPER et al), which is hereby duly incorporated by reference.

Unless otherwise stated, references herein to "the drug(s)" relates to lopinavir and ritonavir either in combination or individually.

In a particular embodiment, oil in water formation comprises:
(i) providing an oil phase comprising the drug(s);
(ii) providing an aqueous phase comprising the hydrophilic polymer and surfactant; and
(iii) mixing the oil phase and aqueous phase to produce the oil in water emulsion.

Suitably, the oil phase is provided by dissolving the drug(s) in a suitable organic solvent. Each of lopinavir and ritonavir may be dissolved separately in a suitable organic solvent (optionally different organic solvents) and subsequently mixed to form the oil phase.

Suitably, the aqueous phase is provided by dissolving hydrophilic polymer and surfactant in an aqueous medium, preferably in water. Alternatively the aqueous phase may be provided by mixing two separately prepared aqueous solutions of the surfactant and hydrophilic polymer.

In a particular embodiment, further aqueous medium (e.g. water) or organic solvent is added before or during mixing step (iii).

The concentration of drug(s) in the oil in water emulsion is suitably as concentrated as possible to facilitate effective scale-up of the process. For example, the concentration of drug(s) in the oil phase is suitably 20 mg/ml or higher, more suitably 40 mg/ml or higher, even more suitably greater than 60 mg/ml or higher.

The concentration of the hydrophilic polymer in the aqueous/water phase is suitably 0.5-50 mg/mL.

The concentration of the surfactant in the aqueous/water phase emulsion is suitably 0.5 to 50 mg/mL.

The organic solvent forming the oil phase is (substantially) immiscible with water. Suitably the organic solvent is aprotic. Suitably the organic solvent has a boiling point less than 120° C., suitably less than 100° C., suitably less than 90° C.

In a particular embodiment, the organic solvent is a selected from the Class 2 or 3 solvents listed in the International Conference on Harmonization (ICH) guidelines relating to residual solvents.

In a particular embodiment, the organic solvent is selected from chloroform, dichloromethane, dichloroethane, tetrachloroethane, cyclohexane, hexane(s), isooctane, dodecane, decane, methylbutyl ketone (MBK), methylcyclohexane, tetrahydrofuran, toluene, xylene, butyl acetate, mineral oil, tert-butylmethyl ether, heptanes(s), isobutyl acetate, isopropyl acetate, methyl acetate, methylethyl ketone, ethyl acetate, ethyl ether, pentane, and propyl acetate, or any suitably combination thereof.

In a particular embodiment, the organic solvent is selected from chloroform, dichloromethane, methylethylketone (MEK), methylbutylketone (MBK), and ethyl acetate.

The volume ratio of aqueous phase to oil phase in mixing step (iii) is suitably between 20:1 and 1:1, more suitably between 10:1 and 1:1, and most suitably between 6:1 and 2:1.

Mixing step (iii) suitably produces a substantially uniform oil in water emulsion. As previously indicated, mixing may be performed using methods well known in the art. Suitably, mixing step (iii) involves stirring, sonication, homogenisation, or a combination thereof. In a particular embodiment, mixing step (iii) involves sonication and/or homogenisation.

Removing the oil and water may be performed using methods well known in the art. Suitably removing the oil and water involves freeze drying, spray drying or spray granulation.

Removing the oil and water may be performed using methods described in WO 2004/011537 A1 (COOPER et al), the entire contents of which are hereby incorporated by reference.

In a particular embodiment, removing the oil and water involves freeze drying the oil in water emulsion. As such, removing the oil and water may suitably comprise freezing the oil in water emulsion and then removing the solvents under vacuum.

Preferably, the freezing of the oil in water emulsion may be performed by externally cooling the oil in water emulsion. For example, a vessel containing the oil in water emulsion may be externally cooled, for example, by submerging the vessel in a cooling medium, such as liquid nitrogen. Alternatively the vessel containing the oil in water emulsion may be provided with an external "jacket" through which coolant is circulated to freeze the oil in water emulsion. Alternatively the vessel may comprise an internal element through which coolant is circulated in order to freeze the oil in water emulsion.

In a further alternative, the oil in water emulsion is frozen by being contacted directly with a cooling medium at a temperature effective for freezing the emulsion. In such cases, the cooling medium (e.g. liquid nitrogen) may be added to the oil in water emulsion, or the oil in water emulsion may be added to the cooling medium. In a particular embodiment, the oil in water emulsion is added to the fluid medium (e.g. liquid nitrogen), suitably in a dropwise manner. This order of addition provides higher purities of final product. As such, frozen droplets of the oil in water emulsion may suitably form. Such frozen droplets may suitably be isolated (e.g. under vacuum to remove the fluid medium/liquid nitrogen). The solvent is then suitably removed from the frozen droplets under vacuum. The resulting solid composition (or LPV or RTV solid products, depending on the process used) is then isolated.

In processes where separate LPV and RTV solid products require blending to produce the solid composition, the blending may suitably employ methods well known in the art. Blending suitably provides a substantially homogeneous solid composition.

In an alternative aspect, the present invention provides a process for preparing a solid composition as defined herein, the process comprising:

preparing a single phase solution comprising lopinavir and ritonavir, a hydrophilic polymer as defined herein, and a surfactant as defined herein, in one or more solvents; and spray-drying the mixture to remove the one or more solvents to form the solid composition.

In this aspect of the invention, the single phase solution comprising the lopinavir and ritonavir, hydrophilic polymer, and surfactant are all dissolved in one solvent or two or more miscible solvents. Such processes are well described in WO 2008/006712, the entire contents of which are duly incorporated herein by reference. WO 2008/006712 also lists suitable solvents and combinations thereof for forming the single phase solution. In an embodiment, the single phase solution comprises two or more solvents (e.g. ethanol and water) which together solubilise lopinavir and ritonavir, hydrophilic polymer, and the surfactant. In another embodiment, the single phase comprises a single solvent, for example ethanol or water. Removing of the one or more solvents from the single phase fluid mixture involves spray drying—again WO 2008/006712 details suitable spray-drying conditions.

The present invention also provides a solid composition obtainable by, obtained by, or directly obtained by any of the processes described herein.

Aqueous Dispersion of Liponavir and Ritonavir Nanoparticles

The present invention provides an aqueous dispersion, comprising a plurality of nanoparticles of lopinavir and ritonavir dispersed in an aqueous medium, the nanoparticles comprising a core of lopinavir and/or ritonavir and a coating of a hydrophilic polymer and a surfactant;

wherein each core either comprises a mixture of lopinavir and ritonavir, or consists essentially of either lopinavir or ritonavir;

wherein the hydrophilic polymer is selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof; and wherein the surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof.

The present invention also provides an aqueous dispersion, obtainable by, obtained by, or directly obtained by dispersing the solid composition as defined herein in an aqueous medium. Suitably, an aqueous dispersion is prepared immediately prior to use.

When the solid composition is dispersed in the aqueous medium, the hydrophilic polymer and/or surfactant is dissolved within the aqueous medium to release the nanoparticles of lopinavir and ritonavir in a dispersed form. The nanoparticles of lopinavir and ritonavir, which were formerly dispersed within a solid mixture of the hydrophilic polymer and surfactant, then become dispersed within the aqueous medium in a coated form, whereby the cores of lopinavir and ritonavir are each individually coated with the hydrophilic polymer and surfactant. Such a coating is thought to impart stability to the nanoparticles, thereby preventing premature coagulation and aggregation.

As explained in relation to the solid composition, the nanoparticles of lopinavir and ritonavir collectively comprise a mixture of lopinavir and ritonavir, though individual nanoparticle cores may comprise both lopinavir and ritonavir, may consist essentially of lopinavir, or may consist essentially of ritonavir.

In a particular embodiment, individual nanoparticles comprise a core of both lopinavir and ritonavir.

In another embodiment, individual nanoparticles comprise either a core consisting essentially of lopinavir or a core consisting essentially of ritonavir.

In a particular embodiment, the nanoparticles of lopinavir and ritonavir comprise a mixture of individual nanoparticles with cores comprising both lopinavir and ritonavir, individual nanoparticles with cores consisting essentially of lopinavir, and/or individual nanoparticles with cores consisting essentially of ritonavir.

Suitably the relative amounts (including ratios) of lopinavir and ritonavir, hydrophilic polymer, and surfactant are the same as defined in relation to the solid composition. However, their respective wt % values in the aqueous dispersion as a whole must be adjusted to take account of the aqueous medium. In a particular embodiment, the aqueous medium comprises 20 to 99.5 wt % of the total aqueous dispersion. In a particular embodiment, the aqueous medium comprises 50 to 98 wt % of the total aqueous dispersion. In a particular embodiment, the aqueous medium comprises 70 to 95 wt % of the total aqueous dispersion. Suitably, the remaining proportion of the aqueous dispersion essentially consists of lopinavir and ritonavir, hydrophilic polymer, and surfactant, whose proportions within the aqueous dispersion as a whole are accordingly calculated (and scaled) by reference to the proportions recited in relation to the solid composition.

In a particular embodiment, the aqueous medium is water. In an alternative embodiment, the aqueous medium comprises water and one or more additional pharmaceutically acceptable diluents or excipients.

Aqueous dispersions of the present invention are advantageously stable for prolonged periods, both in terms of chemical stability and the stability of the particles themselves (i.e. with respect to aggregation, coagulation, etc.).

Aqueous dispersions of the present invention may be considered as pharmaceutical compositions of the present invention.

Aqueous dispersions of the present invention allow a measured aliquot to be taken therefrom for accurate dosing in a personalised medicine regime.

The particle size, polydispersity and zeta potential of the nanoparticles of lopinavir and ritonavir in the aqueous dispersion is as defined hereinbefore in relation to the solid composition. It will of course be appreciated that the particle size, polydispersity and zeta potential nanoparticles of lopinavir and ritonavir present in the solid composition are measured by dispersing the solid composition in an aqueous medium to thereby form an aqueous dispersion of the present invention.

Process for Preparing an Aqueous Dispersion

The aqueous dispersion may be formed by methods well known in the art. For example, lopinavir and ritonavir may be milled in the presence of an aqueous mixture of the hydrophilic polymer and surfactant.

In a particular aspect of the invention, however, there is provided a process for preparing an aqueous dispersion, comprising dispersing a solid lopinavir and ritonavir composition as defined herein in an aqueous medium.

In a particular embodiment, the aqueous medium is water. In an alternative embodiment, the aqueous medium comprises water and one or more additional excipients.

Dispersing the solid composition in the aqueous medium may comprise adding the solid composition to an aqueous medium and suitably agitating the resulting mixture (e.g. by shaking, homogenisation, sonication, stirring, etc.).

Solid Ritonavir Composition

The present invention also provides a solid ritonavir (RTV) composition, comprising nanoparticles of ritonavir dispersed within a mixture of at least one hydrophilic polymer and at least one surfactant;

wherein the hydrophilic polymer is selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof; and wherein the surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof.

The nanoparticles of ritonavir drug substances are dispersed within a solid excipient mixture comprising the hydrophilic polymer and the surfactant as previously defined herein for the liponavir/ritonavir solid compositions. The properties of the nanoparticles of ritonavir (particle size, zeta potential, polydispersity etc.) are the same as those defined previously herein for the liponavir and ritonavir solid compositions defined herein.

The surfactant and hydrophilic polymer and particular combinations thereof are as defined hereinbefore for the liponavir and ritonavir solid compositions defined herein.

The formulation of the solid RTV compositions of the invention is the same as described herein for the liponavir and retanovir solid compositions.

In an embodiment, the solid composition comprises one surfactant and one hydrophilic polymer selected from those recited herein.

Processes for Preparing the Solid Ritonavir Composition

The solid ritonavir compositions may be prepared by any of the techniques defined hereinbefore for the solid compositions of liponavir and ritonavir. For example, the solid ritonavir composition may be prepared by milling a solid form of ritonavir as described hereinbefore. However, it is generally preferred that the solid ritonavir compositions of the present invention are prepared by an oil-in-water emulsion technique whereby the ritonavir is dissolved in the oil phase and the hydrophilic polymer and surfactant are present in the water phase. The oil and water solvents are then removed by freeze drying, spray drying or spray granulation to provide a solid composition according to the invention.

Thus, in accordance with one aspect of the present invention, there is provided a process for preparing a solid ritonavir composition as defined herein, the process comprising:
  (a) preparing an oil in water emulsion comprising:
    an oil phase comprising ritonavir; and
    an aqueous phase comprising a hydrophilic polymer and a surfactant, each as defined herein; and
  (b) removing the oil and water from the oil in water emulsion to form the solid composition.

Further details of such process are defined above in relation to the solid composition of liponavir and ritonavir.

Aqueous Dispersion of Ritonavir Nanoparticles

The present invention also provides an aqueous dispersion, comprising a plurality of nanoparticles of ritonavir dispersed in an aqueous medium, the nanoparticles comprising a core of ritonavir and a coating of at least one hydrophilic polymer and at least one surfactant;
  wherein the hydrophilic polymer is selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof; and
  wherein the surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof.

The present invention also provides an aqueous dispersion, obtainable by, obtained by, or directly obtained by dispersing the solid ritonavir composition as defined herein in an aqueous medium.

The particle size, polydispersity and zeta potential of the nanoparticles of ritonavir in the aqueous dispersion is as defined hereinbefore.

Process for Preparing an Aqueous Dispersion

The aqueous ritonavir dispersion may be formed by methods described previously for the aqueous dispersion of liponavir/ritonavir nanoparticles. Such methods are well known in the art. For example, ritonavir may be milled in the presence of an aqueous mixture of the hydrophilic polymer and surfactant.

In a particular aspect of the invention, however, there is provided a process for preparing an aqueous dispersion, comprising dispersing a solid ritonavir composition as defined herein in an aqueous medium.

In a particular embodiment, the aqueous medium is water. In an alternative embodiment, the aqueous medium comprises water and one or more additional excipients.

Dispersing the solid composition in the aqueous medium may comprise adding the solid composition to an aqueous medium and suitably agitating the resulting mixture (e.g. by shaking, homogenisation, sonication, stirring, etc.).

Pharmaceutical Compositions

The present invention provides a pharmaceutical composition comprising a solid composition or an aqueous dispersion as defined herein. The pharmaceutical compositions of the present invention may further comprise one or more additional pharmaceutically acceptable excipients.

The solid compositions of the invention may be formulated into a form suitable for oral use (for example as tablets, lozenges, hard or soft capsules, or dispersible powders or granules) by techniques known in the art. As such, the solid compositions of the invention may be mixed with one or more additional pharmaceutical excipients during this process, such as antiadherants, binders, coatings, enterics, disintegrants, fillers, diluents, flavours, colours, lubricants, glidants, preservatives, sorbents, and sweeteners.

In a particular embodiment, the pharmaceutical composition is a tablet or capsule comprising the solid lopinavir and ritonavir composition.

The aqueous dispersion of the present invention may be administered as it is or further formulated with one or more additional excipients to provide a dispersion, elixir or syrup that is suitable for a oral use, or a dispersion that is suitable for parenteral administration (for example, a sterile aqueous dispersion for intravenous, subcutaneous, intramuscular, intraperitoneal or intramuscular dosing).

In a particular embodiment, the pharmaceutical composition is an aqueous dispersion as described herein. Such dispersed formulations can be used to accurately measure smaller dosages, such as those suitable for administration to children.

In a particular embodiment, the pharmaceutical composition is in a form suitable for parenteral delivery, whether via intravenous or intramuscular delivery.

It will be appreciated that different pharmaceutical compositions of the invention may be obtained by conventional procedures, using conventional pharmaceutical excipients, well known in the art.

The pharmaceutical compositions of the invention contain a therapeutically effective amount of lopinavir and ritonavir.

A person skilled in the art will know how to determine and select an appropriate therapeutically effective amount of lopinavir and ritonavir to include in the pharmaceutical compositions of the invention.

Uses of the Nanoparticles Formulation and Pharmaceutical Composition

The present invention provides a solid composition or an aqueous dispersion as defined herein for use as a medicament.

In principle, the solid composition or aqueous dispersion defined herein can be used for the treatment of any virus that comprises a protease enzyme.

The present invention further provides a solid composition or an aqueous dispersion as defined herein for use in the treatment and/or prevention of retroviral infections (e.g. HIV).

The present invention further provides a use of a solid composition or an aqueous dispersion as defined herein in the manufacture of a medicament for use in the treatment and/or prevention of retroviral infections (e.g. HIV).

The present invention further provides a method of treating and/or preventing a retroviral infection (e.g. HIV), the method comprising administering a therapeutically effective amount of a solid composition, an aqueous dispersion, or a pharmaceutical composition as defined herein, to a patient suffering from or at risk of suffering from a retroviral infection.

The term "retrovirus" generally refers to an RNA virus capable of self-duplication in a host cell using the reverse transcriptase enzyme to transcribe its RNA genome into DNA. The DNA is then potentially incorporated into the host's genome so that the virus can then replicate thereafter as part of the host's DNA.

The retroviral infection to be treated or prevented is suitably selected from human immunodeficiency virus (HIV), Alpharetrovirus, Betaretrovirus, Gammaretrovirus, Deltaretrovirus, Epsilonretrovirus, Lentivirus, Spumavirus, Metavirus, Errantvirus, Pseudovirus, Hepadnavirus, and Caulimovirus.

In a particular embodiment of the present invention, the retroviral infection to be treated or prevented is the human immunodeficiency virus (HIV), most suitably the human immunodeficiency virus (HIV) type 1.

The solid compositions, aqueous dispersions, and pharmaceutical compositions of the present invention are suitably used as part of highly antiretroviral therapy (HAART) in the treatment of human immunodeficiency virus (HIV) type 1.

The solid compositions, aqueous dispersions, and pharmaceutical compositions of the present invention are also suitably used to reduce the risk of or prevent HIV infection developing in subjects exposed to a risk of developing HIV infection.

Lopinavir and ritonavir, the active agents in the solid compositions, aqueous dispersions, and pharmaceutical compositions of the present invention, are antiretroviral drugs which act together as protease inhibitors. As such, the solid composition, aqueous dispersion, and pharmaceutical compositions of the present invention are capable of inhibiting protease activity. Moreover, the nanoparticles and pharmaceutical compositions of the present invention are suitable for use in antiretroviral therapies and prophylactic treatments.

Thus in another aspect of the invention there is provided a method of inhibiting protease activity in a cell (in vivo or in vitro), the method comprising administering to said cell a solid composition, aqueous dispersion, or pharmaceutical composition as described herein.

In another aspect, the present invention provides a method of inhibiting protease activity in a human or animal subject in need of such inhibition, the method comprising administering to said subject an effective amount of a solid composition, aqueous dispersion, or pharmaceutical composition as defined herein.

In another aspect, the present invention provides a solid composition, aqueous dispersion, or pharmaceutical composition as defined herein for use in the treatment of a disease or condition associated with protease activity.

In another aspect, the present invention provides the use of a solid composition, aqueous dispersion, or pharmaceutical composition as defined herein in the manufacture of a medicament for use in the treatment of a disease or condition associated with protease activity.

Liponavir has also been shown to possess some activity against malaria. Thus, in yet another aspect, the solid composition or aqueous dispersion defined herein can be used for the treatment of malaria.

Routes of Administration

The solid compositions, aqueous dispersions, and pharmaceutical compositions of the invention may be administered to a subject by any convenient route of administration.

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, infraarterlal, intracardiac, intrathecal, intraspinal, intracapsular, subcapsular, intraorbital, intraperitoneal, intratracheal, subcuticular, intraarticular, subarachnoid, and intrasternal; or by implant of a depot or reservoir, for example, subcutaneously or intramuscularly.

In a particular embodiment (e.g. in HIV treatments), the route of administration is either oral or by implant of a depot or reservoir formulation.

Combination Therapy

Although it is possible that the solid compositions, aqueous dispersions, and pharmaceutical compositions of the invention may be used as a sole medicament in the treatment and/or prevention of a retrovirus infection such as HIV, they may also be used in combination with one or more additional anti-retroviral and/or anti-microbial agents.

Other antiretroviral agents suitable in combination treatments with the formulations and compositions of the present invention include Zidovudine, Zalcitabine, Didanosine, Stavudine, Lamivudine, Abacavir, Combivir (zidovudine+lamivudine), Trizivir (zidovudine+lamivudine+abacavir), Tenofovir, Emtricitabine, Truvada (Tenofovir+Emtricitabine), Epzicom/Kivexa (abacavir+lamivudine), Hydroxyurea, Nevirapine, Delavirdine, Etravirine, Rilpivirine, Atripla (lopinavir+emtricitabine+tenofovir), Indinavir, Ritonavir, Saquinavir, Nelfinavir, Amprenavir, Kaletra (lopinavir+ritonavir), Atazanavir, Fosamprenavir, Tipranavir, Darunavir, Enfuvirtide, Maraviroc, Raltegravir, Nevirapine, Efavirenz, Delavirdine, Etravirine, Rilprivrine, Artipla, or combinations thereof.

In a particular embodiment, the other suitable antiretroviral agents suitable for use in combination treatments with the formulations and compositions of the present invention include Tenofovir, Lamivudine, Abacavir, Emtricitabine, Zidovudine, Combivir (zidovudine+lamivudine), Truvada (Tenofovir+Emtricitabine), Epzicom/Kivexa (abacavir+lamivudine), or combinations thereof.

In a preferred embodiment, the other antiretroviral agents suitable for use in combination treatments with the formulations and compositions of the present invention include two of the following: Tenofovir, Lamivudine, Abacavir, Emtricitabine, Didanosine, Zidovudine.

In particular embodiments, the other antiretroviral agents suitable in combination with formulations and compositions of the present invention are themselves provided as combinations such as:

Emtricitabine+Tenofovir disoproxil fumarate
Lamivudine+Stavudine
Lamivudine+Tenofovir disoproxil fumarate
Lamivudine+Zidovudine
Lamivudine+Didanosine.

It is envisaged that the ritonavir solid composition and aqueous dispersion defined herein, will be only be used in combination with other anti-retroviral agents, in particular liponavir.

Accordingly, an aspect of the invention provides a combination suitable for use in the treatment or prevention of a retrovirus infection, such as HIV, comprising a solid composition, an aqueous dispersion, or a pharmaceutical composition as defined hereinbefore, and one or more other antiretroviral agents.

The present invention also provides a solid composition, an aqueous dispersion, or a pharmaceutical composition as defined hereinbefore for use in the treatment or prevention of a retrovirus infection, such as HIV, wherein the solid composition, aqueous dispersion, or pharmaceutical composition is administered in combination with one or more other antiretroviral agents.

In a further aspect, the present invention provides a pharmaceutical composition comprising a solid composition as defined herein and one or more additional antiretroviral agents.

In a further aspect, the present invention provides a pharmaceutical composition comprising an aqueous dispersion as defined herein which further comprises one or more additional antiretroviral agents.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

Such conjoint treatment may be achieved by way of the simultaneous, sequential or separate dosing of the individual components of the treatment. Such combination products employ the formulations or compositions of this invention within the dosage range described hereinbefore and the other pharmaceutically-active agent within its approved dosage range.

In a further aspect of the invention, there is provided a pharmaceutical composition comprising a solid composition or an aqueous dispersion as defined herein; and one or more other antiretroviral agents. In a particular embodiment, the pharmaceutical composition is a single dosage form.

Kit of Parts

The present invention provides a kit of parts comprising a solid composition as defined herein or pharmaceutical composition comprising the solid composition as defined herein, and a pharmaceutically acceptable aqueous diluent.

The solid composition or pharmaceutical composition comprising the solid composition as defined herein can be dispersed into the diluent to provide an aqueous dispersion as defined herein. Either the entire dispersion can then be administered, or a proportion of it can be measured and then administered (thereby providing a means of administering different dosages to individual patients).

EXAMPLES

Materials

All materials were purchased and used without further purification from Sigma-Aldrich unless specified otherwise.

Example 1

Synthesis of Lopinavir and Ritonavir Combination Particles

Samples are prepared using a 70 mgml$^{-1}$ stock solution of lopinavir and ritonavir (A) in chloroform (at either 4:1, 8:1 or 40:1 mass ratios of LPV to ritonavir), a 22.5 mgml$^{-1}$ of PVA (P) and a 22.5 mgml$^{-1}$ stock solution of Vit-E-PEG-succinate (S). Stock solutions are added in the following proportion; 100 µl (A); 90 µl (P) 45 µl (S) and 265 µl of water, therefore solid mass ratio is; 70% (A), 20% (P) and 10% (S) in an 1:4 oil to water (O/W) mix. The mixtures are the emulsified using a Covaris S2x for 30 seconds with a duty cycle of 20, an intensity of 10 and 500 cycles/burst in frequency sweeping mode. After which, the samples were immediately cryogenically frozen. Three samples (where the LPV to RTV ratio was 4:1, 8:1 or 40:1) were prepared. Once all 3 samples had been prepared, they were lyophilised (Virtis benchtop K) for 42 hours to leave a dry porous product. The samples were then sealed in individual vials until analysis.

FIG. 1 shows a 3-D bar chart displaying the z-average particle size for the three lopinavir and ritonavir combination ratios.

Figure 2:
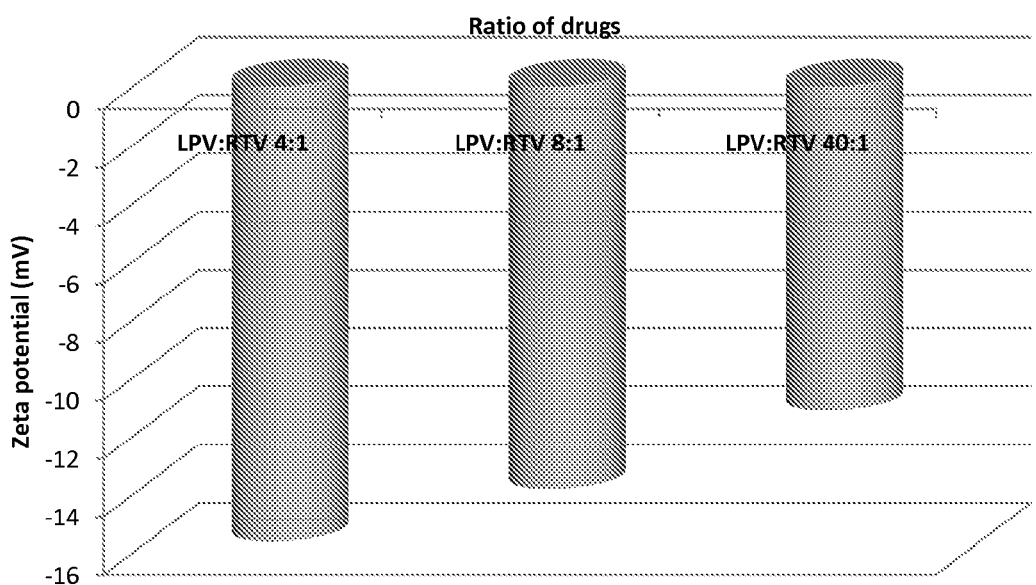
FIG. 2 shows a 3-D bar chart displaying the zeta potentials of the particles the three lopinavir and ritonavir combination ratios prepared in Example 1.

FIG. 2 shows a 3-D bar chart displaying the zeta potentials of the particles the three lopinavir and ritonavir combination ratios.

Example 2

Synthesis of Radiolabelled Lopinavir and Ritonavir Combination Particles

Radiolabelled lopinavir and ritonavir samples were prepared in accordance with the method previously described in Example 1, however, the chloroform solution containing the lopinavir and ritonavir was also dosed with either radiolabelled lopinavir or ritonavir to give a tracer concentration of radioactivity for combination samples.

Example 3

Screening for Nanoformulations of Ritonavir—10 Hydrophilic Polymers, 16 Surfactants Samples are prepared using a 10 mgml$^{-1}$ stock solution of ritonavir (A) in chloroform, a 22.5 mgml$^{-1}$ of polymer (P)

and a 22.5 mgml$^{-1}$ stock solution of surfactant (S). Stock solutions are added in the following proportion; 100 μl (A); 267 μl (P) and 133 μl (S), therefore solid mass ratio is; 10% (A), 60% (P) and 30% (S) in an 1:4 oil to water (O/W) mix. The mixtures are then emulsified using a probe sonicator (UP400S manufactured by Hielscher (Germany)), fitted with an H3 titanium probe) operated at 20% amplitude for 7 seconds followed by immediate cryogenic freezing.

A matrix of 160 samples (comprised of 10 different polymers and 16 surfactants) was prepared. Once all 160 samples had been prepared, they were lyophilised (Virtis benchtop K) for 42 hours to leave a dry porous product, the samples were then sealed in individual vials until analysis.

The polymers and surfactants employed in this screen are detailed in Table 1A and Table 1B below:

TABLE 1A

List of hydrophilic polymers initially screened

| Polymer | MW | m/dm$^3$ (22.5 mg/ml) |
|---|---|---|
| PEG 1k | 1000 | 0.00225 |
| F68 | 8400 | 0.000267857 |
| F127 | 12600 | 0.000178571 |
| Kollicoat | 45000 | 0.00005 |
| PVA | 9500 | 0.000236842 |
| PVP k30 | 30000 | 0.000075 |
| HPC | 80000 | 0.000028125 |
| HPMC | 10000 | 0.000225 |
| Hydrolysed gelatin | 1982 | 0.001135217 |
| NaCMC | 90000 | 0.000025 |

TABLE 1B

List of 16 Surfactants initially screened

| Surfactant | MW | m/dm$^3$ (22.5 mg/ml) |
|---|---|---|
| Na alginate | 155000 | 1.45161E−05 |
| Na Myristate | 250.35 | 0.008987418 |
| Na Deoxycholate | 414.55 | 0.005427572 |
| Na Caprylate | 166.19 | 0.013538721 |
| Vit E-peg-succinate | 1000 | 0.00225 |
| Sisterna 11 | 650 | 0.003461538 |
| Sisterna 16 | 650 | 0.003461538 |
| SDS | 288.38 | 0.007802205 |
| AOT | 444.56 | 0.005061184 |
| Chremophor EL | 2500 | 0.0009 |
| Solutol HS | 344.53 | 0.006530636 |
| Tween 20 | 1227 | 0.001833741 |
| Tween 80 | 1300 | 0.001730769 |
| Brij 58 | 1123.52 | 0.002002635 |
| Hyamine | 448.08 | 0.005021425 |
| CTAB | 364.46 | 0.006173517 |

Screen Analysis

Immediately prior to analysis, samples were dispersed by addition of 1 ml of water. The particle size of the active, organic nanoparticulate dispersion is then measured by dynamic light scattering (DLS) using a Malvern Zetasizer Nano ZS. 3 measurements using automatic measurement optimisation, Malvern Zetasizer software version 6.20 was used for data analysis. The particles were considered hits if the below criteria were met.

Nanodispersion Quality Assessment Criteria

A particle is determined a hit if it complies with the following criteria: Complete dispersion of the sample with no large particles visible, a particle Z-average <1000 nm, a polydispersity index (PDI)<0.5, a standard deviation between three scans <10% from average Z-average and two of the three DLS scans pass the size quality report. The size quality report incorporates 12 tests on the reliability of the data recorded and is automatically applied to each measurement by the Malvern Zetasizer software. These tests ensure that the sample is within a size range appropriate for DLS, has a PDI below 1, is within the correct concentration range and that the cumulant and distribution fit are good (i.e. the errors on the data are less than 0.005).

Table 1C below lists the hits in terms of suitable hydrophilic polymers and surfactants.

TABLE 1C hits of suitable hydrophilic polymers and surfactants (68 hits in all)

| Hydrophilic Polymer | Surfactant |
|---|---|
| PEG 1K | Na Deoxycholate. |
| PEG 1K | Na caprylate. |
| PEG 1K | AOT |
| PEG 1K | Chremophor EL |
| PEG 1K | Tween 20 |
| Pluronic F68 | Na Deoxycholate. |
| Pluronic F68 | AOT |
| Pluronic F68 | Chremophor EL |
| Pluronic F68 | Tween 20 |
| Pluronic F68 | Tween 80 |
| Pluronic F68 | Brij 58 |
| Pluronic F127 | Na Deoxycholate. |
| Pluronic F127 | Na caprylate. |
| Pluronic F127 | AOT |
| Pluronic F127 | Tween 20 |
| Pluronic F127 | Tween 80 |
| Pluronic F127 | Hyamine |
| Kollicoat | Na Deoxycholate. |
| Kollicoat | Na caprylate. |
| Kollicoat | Vit E-peg-succinate |
| Kollicoat | Sisterna 16 |
| Kollicoat | AOT |
| Kollicoat | Chremophor EL |
| Kollicoat | Solutol HS |
| Kollicoat | Tween 20 |
| Kollicoat | Tween 80 |
| Kollicoat | Brij 58 |
| Kollicoat | Hyamine |
| PVA | Na Deoxycholate. |
| PVA | Vit E-peg-succinate |
| PVA | Sisterna 11 |
| PVA | Sisterna 16 |
| PVA | AOT |
| PVA | Chremophor EL |
| PVA | Solutol HS |
| PVA | Tween 20 |
| PVA | Tween 80 |
| PVA | Brij 58 |
| PVA | Hyamine |
| PVP 30K | Na Deoxycholate. |
| PVP 30K | Na caprylate. |
| PVP 30K | Vit E-peg-succinate |
| PVP 30K | AOT |
| PVP 30K | Chremophor EL |
| PVP 30K | Solutol HS |
| PVP 30K | Tween 20 |
| PVP 30K | Tween 80 |
| PVP 30K | Brij 58 |
| PVP 30K | Hyamine |
| HPC | Na caprylate. |
| HPC | AOT |
| HPC | Tween 20 |
| HPC | Tween 80 |
| HPC | CTAB |
| HPMC | AOT |
| HPMC | Chremophor EL |
| HPMC | Solutol HS |
| HPMC | Tween 20 |
| HPMC | Tween 80 |
| HPMC | CTAB |

TABLE 1C-continued hits of suitable hydrophilic polymers and surfactants (68 hits in all)

| Hydrophilic Polymer | Surfactant |
|---|---|
| Hydrolysed gelatine | Na caprylate. |
| Hydrolysed gelatine | Vit E-peg-succinate |
| Hydrolysed gelatine | AOT |
| Hydrolysed gelatine | Chremophor EL |
| Hydrolysed gelatine | Solutol HS |
| Hydrolysed gelatine | Tween 80 |
| Hydrolysed gelatine | Hyamine |
| NaCMC | Chremophor EL |

Example 4

Cytotoxicity of Lopinavir/Ritonavir Combination Nanodispersions in Primary Hepatic, Monocyte, Macrophage and Lymphocyte Cells Cell Treatment Cryopreserved Human Primary Hepatocytes.

Cryopreserved human primary hepatocytes (Lonza, USA) were removed from liquid $N_2$ and rapidly warmed to 37° C. then transferred into a conical centrifuge tube containing Hepatocyte Complex Media (HCM: containing; ascorbic acid (0.1% v/v), transferin (0.1% v/v), human recombinant growth factor (rhEGF) (0.1% v/v), insulin (0.1% v/v), gentamycin sulphate amphotericin (0.1% v/v), hydrocortisone 21 hemisuccinate (0.1% v/v) and bovine serum albumin (BSA-FAF (fatty acid free: FAF) (2% v/v)) supplemented with 2% sterile filtered foetal bovine serum (FBS: Bio-Whittaker, Berkshire, UK). The resulting cell suspension was then centrifuged at 50×g and 4° C. for 3 minutes (Heraeus Multifuge 3SR+; Thermo Scientific, UK). The cell pellet was then resuspended in 10 ml HCM and a subsequent trypan blue exclusion assay showed these cells to be 97% viable. The cell density was then adjusted to give $1 \times 10^5$ cells/ml. 100 μl of this cell suspension was then dispensed into each well of a 96 well plate (Nunclon™, Denmark) and incubated for 3 hours at 37° C. and 5% $CO_2$. Media was then aspirated and replaced with 100 μl HCM without 2% FBS.

Cryopreserved Human Immune Cells.

Vials containing cryopreserved peripheral blood (CD14+, CD4+ and natural killer (CD56+)) cells (Lonza, Switzerland) were individually removed from liquid $N_2$ and rapidly thawed in a 37° C. water bath. The cells were then separately transferred into pre-warmed (37° C.) RPMI 1640 supplemented with 10% sterile filtered foetal bovine serum (FBS; Bioclear, UK) and 20 U/ml DNase I (Sigma, UK). The cell suspension was then centrifuged at 200×g at room temperature for 15 minutes. The supernatant was aspirated and the cell pellet resuspended in 2 ml RPMI 1640 and 10% sterile filtered FBS and viability determined by trypan blue exclusion assay. The cells were then rested for 1 hour at 37° C. and 5% $CO_2$ prior to use with routine cell culture, cytotoxicity and cellular accumulation assays. Peripheral blood CD14+ cells were differentiated into monocyte-derived macrophages (MDM) by suspending at a density of $2.5 \times 10^5$ cells/ml in lymphocyte growth media-3 (LGM-3) (Lonza, Switzerland) supplemented with 20% human AB serum (Lonza, Switzerland), 20 U/ml DNase I (Sigma, UK) and 10 ng/ml granulocyte-macrophage colony-stimulating factor (Sigma, UK) then incubated at 37° C. and 5% $CO_2$ for 7 days prior to use.

ATP Cell Viability Assay (Promega: CellTiter-Glo@ Luminescent)

Prior to starting viability assays, all reagents were made fresh and in accordance to manufacturer's instructions and allowed to equilibrate to room temperature immediately before use. After 24 hours incubation, 96 well plates were removed from the incubator and the plate and its contents allowed too equilibrate to room temperature for approximately 30 minutes. After 30 minutes, 80 μl of media was aspirated from each individual well and 20 μl CellTiter-Glo® Reagent (Promega, UK) was added to the remaining media and cells. The contents were then mixed for 2 minutes on an orbital shaker to induce cell lysis. The plate was then further incubated at room temperature for 10 minutes to stabilise luminescent signal. Luminescence was then measured using a Tecan Genios plate reader (Tecan; Austria).

Table 2 provides data in relation to the cytotoxicity of the various 70% drug loaded lopinavir/ritonavir combination formulations in terms of $IC_{50}$ (μM).

TABLE 2

Cytotoxicity of 70% loaded lopinavir/ritonavir nanodispersions and aqueous lopinavir/ritonavir across various primary cell types. Data are given as $IC_{50}$ in μM.

| | Cell line | | | | |
|---|---|---|---|---|---|
| Designation | Primary hepatocytes | Primary CD4+ cells | Primary CD14+ cells | Activated primary CD14+ cells | Primary CD56+ cells |
| Combination Nanodispersion (1:4) | 70.2 | 38.2 | 32.2 | 80.2 | 36.9 |
| Combination Nanodispersion (1:10) | 75.7 | 57.2 | 40.1 | 102.4 | 57.1 |
| Combination Nanodispersion (1:40) | 91.3 | 89.0 | 47.6 | 146.3 | 80.3 |
| Aqueous Combination (1:4) | 19.6 | 12.7 | 11.9 | 22.8 | 10.3 |
| Aqueous Combination (1:10) | 28.8 | 30.8 | 21.0 | 35.4 | 18.3 |
| Aqueous Combination (1:40) | 36.9 | 54.4 | 27.1 | 53.1 | 48.7 |

In summary, all 70% loaded combination nanodispersions were less cytotoxic than equivalent concentrations of aqueous lopinavir/ritonavir.

Example 5

Cellular Accumulation of Combination Lopinavir/Ritonavir Nanodispersions Compared to their Aqueous Equivalents Cellular Accumulation of Combination Nanodispersions of Lopinavir/Ritonavir Compared to their Aqueous Equivalents in Primary Hepatic, Monocyte, Macrophage and Lymphocyte Cells.

Vials containing primary hepatocytes or primary immune cells were removed from liquid $N_2$ and rapidly thawed in a 37° C. water bath and prepared as previously described and maintained in their cell type specific media; Hepatocyte Complex Media (HCM) for hepatocytes, RPMI 1640 and 10% sterile filtered FBS for CD14+, CD4+, natural killer CD56+. Peripheral blood CD14+ cells were differentiated into monocyte-derived macrophages (MDM) and maintained in the complex differentiation media, as described previously, in a 12 well plate (Nunclon™, Denmark) at a density of $2.5 \times 10^6$ cells for 7 days prior to use. After the appropriate amount of resting time post thawing for each cell type, $2.5 \times 10^6$ cells/ml primary hepatocyte or immune cells were separately seeded into each well of a 12 well plate then incubated for 24 hours at 37° C. and 5% $CO_2$. Plates were removed from the incubator and cells and media separately transferred into sterile 1.5 ml microcentrifuge tubes (Sarstedt, UK) and centrifuged at 50×g for 3 minutes at room temperature. Media was aspirated and the cell pellet washed twice with pre-warmed (37° C.) Hanks balanced salt solution (HBSS; Sigma, UK). After the final wash, the HBSS was replaced with pre-warmed (37° C.) HBSS containing either 10 μM (final concentration) aqueous solution of lopinavir/ritonavir (radiolabelled lopinavir; Moravek, USA) or 10 μM (final concentration) lopinavir/ritonavir nanodispersion (radiolabelled lopinavir). The samples were then incubated for 60 minutes at 37° C. and 5% $CO_2$. After 60 minutes, the microcentrifuge tubes were removed from the incubator and centrifuged at 50×g for 1 minute at room temperature to pellet cells. 100 μl of supernatant fraction (extracellular) was removed and placed into an empty 5 ml scintillation vial (Meridian Biotechnologies Ltd; UK) and stored at −20° C. for 24 hours. The remaining supernatant was aspirated and the resulting cell pellet washed twice in ice cold HBSS with centrifugation at 50×g for 3 minutes at 4° C. After the final wash, 100 μl of ice cold tap water was added to the cell pellet, which was then vortexed for 30 seconds and incubated for 24 hours at −20° C. After 24 hours, 100 μl of crude lysate (intracellular) was dispensed into an empty 5 ml scintillation vial. Finally, 4 ml of Ultima Gold liquid scintillation cocktail fluid (Meridian Biotechnologies Ltd; UK) was added to all intracellular and extracellular samples and radioactivity detected as disintegrations per minute (dpm) using a Perkin Elmer 3100TS scintillation counter.

Figure 3:
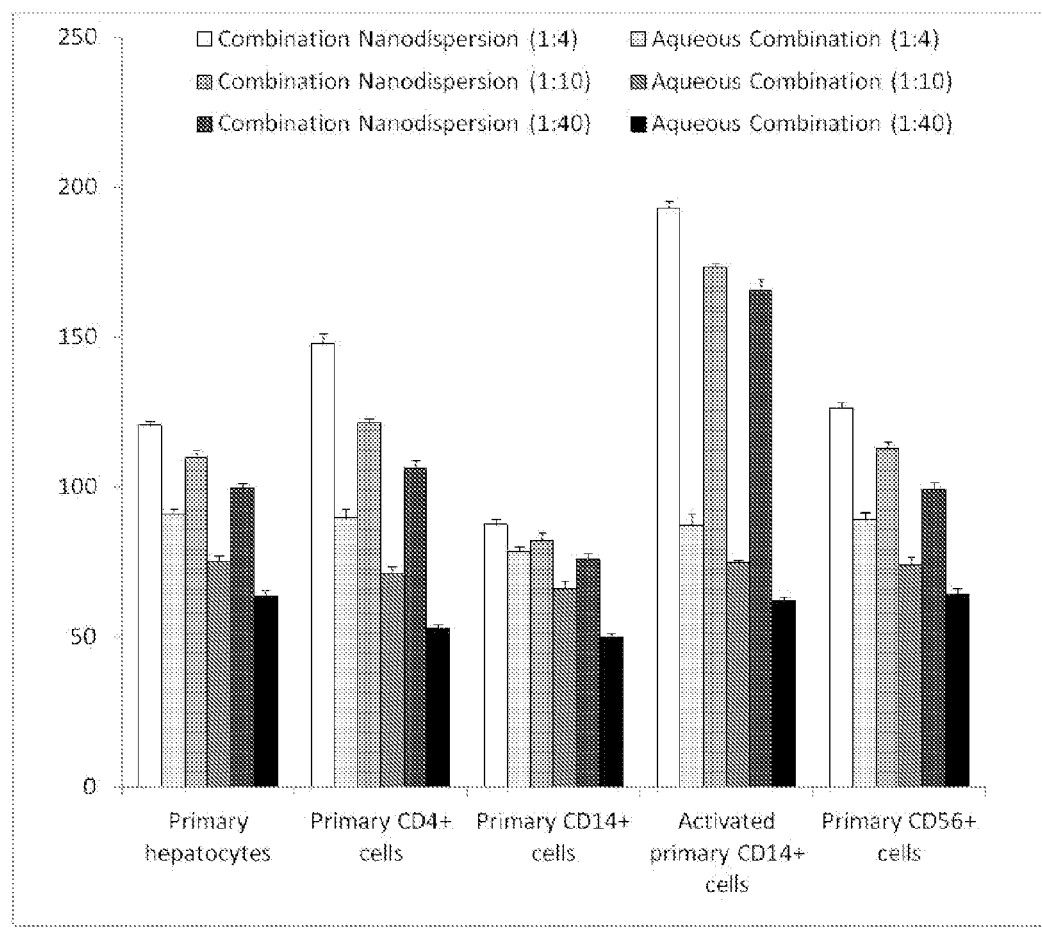
FIG. 3 shows cellular accumulation of 70% loaded lopinavir/ritonavir nanodispersions across various cell types. Data for aqueous lopinavir/ritonavir are also given.

FIG. 3 provides data in relation to the accumulation of the various 70% drug loaded lopinavir/ritonavir combination formulations.

In summary, lopinavir/ritonavir combination nanodispersions which exhibit higher cellular penetration into all cell types studied have been synthesised and characterised. 70% loaded combination nanodispersions with favourable penetration into these cell types have been identified.

Example 6

Transcellular Permeability of Combination Lopinavir/Ritonavir Nanodispersions Across Caco-2 Cell Monolayers For transcellular permeability studies to identify 70% drug loaded lopinavir/ritonavir combination nanodispersion candidates, modelling systemic circulation uptake, Caco-2 cells were propagated to a monolayer over a 21 day period, yielding transepithelial electrical resistance (TEER) values of ~1300Ω. For evaluation of 70% loaded nanodispersions, 10 μM of aqueous or nanoformulated lopinavir (including radiolabelled lopinavir and with ritonavir concentration adjusted for appropriate ratio) was added to the apical chamber of 4 wells and the basolateral chamber of 4 wells to quantify transport in both apical to basolateral and basolateral to apical direction and sampled on an hourly basis over a 4 h time period. Apparent permeability coefficient was determined by the amount of compound transported using the following equation: $P_{app}=(dQ/dt)(1/(AC_0))$. Where (dQ/dt) is the amount per time (nmol·sec$^{-1}$), A is the surface area of the filter and $C_0$ is the starting concentration of the donor chamber (10 μM).

Figure 4:
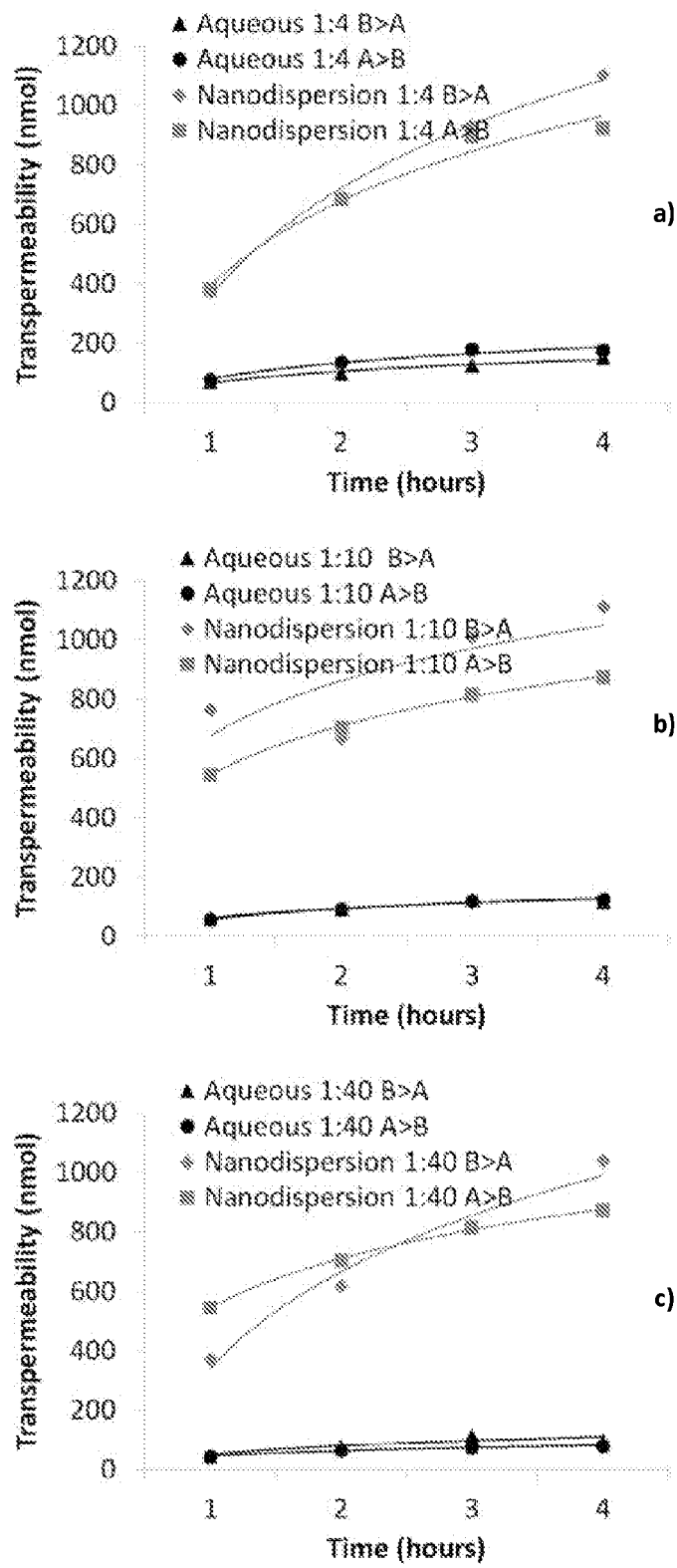
FIG. 4 shows apical to basolateral (A>B) and basolateral to apical (B>A) transcellular permeability of 70% loaded lopinavir/ritonavir combination nanodispersions across Caco-2 cell monolayers. Data for aqueous lopinavir/lopinavir solutions are also given.

FIG. 4 shows apical to basolateral (A>B) and basolateral to apical (B>A) permeability of 70% loaded lopinavir/ritonavir combination nanodispersions.

In summary, 70% loaded lopinavir/ritonavir nanodispersions have been synthesised and characterised that exhibit greater permeability across caco-2 cell monolayers.

CONCLUSION

The lopinavir/ritonavir formulations of the present invention are hereby shown to form stable nanodispersions with a number of favourable pharmacological properties. Nanodispersions have been synthesised that have lower cytotoxicity, that accumulate to a higher degree in target cells and that traverse intestinal epithelial cells more rapidly and more completely than aqueous solutions of lopinavir/ritonavir.

What is claimed is:

1. A solid lopinavir and ritonavir composition, comprising solid nanoparticles of lopinavir and ritonavir dispersed within a solid mixture of at least one hydrophilic polymer and at least one surfactant;
    wherein the hydrophilic polymer is selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof; and
    wherein the surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof.

2. A solid composition according to claim 1, wherein the solid nanoparticles of lopinavir and ritonavir have an average particle size of less than or equal to 1 micron (m).

3. A solid composition according to claim 2, wherein the solid nanoparticles of lopinavir and ritonavir have an average particle size between 100 and 800 nm.

4. A solid composition according to claim 1, wherein the solid nanoparticles of lopinavir and ritonavir have a polydispersity of less than or equal to 0.8.

5. A solid composition according to claim 1, wherein the hydrophilic polymer is selected from PVA, Poloxamer 407, PEG 1K, HPMC, PVP K30, and Poloxamer 188, or a combination thereof.

6. A solid composition according to claim 5, wherein the hydrophilic polymer is PVA.

7. A solid composition according to claim 1, wherein the surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, and polyethyleneglycol-12-hydroxystearate, or a combination thereof.

8. A solid composition according to claim 7, wherein the surfactant is selected from vitamin-E-polyethylene glycol-succinate (Vit-E-PEG-succinate), Polysorbate 20, Polysorbate 80, N-alkyldimethylbenzylammonium chloride (e.g.

commercially available as Hyamine®), sodium deoxycholate, dioctyl sodium sulfosuccinate (e.g. AOT), and polyethyleneglycol-12-hydroxystearate (e.g. Solutol® HS), or a combination thereof.

9. A solid composition according to claim 8, wherein the surfactant is selected from vitamin-E-polyethylene glycol-succinate (Vit-E-PEG-succinate), Polysorbate 20, Polysorbate 80, and sodium deoxycholate.

10. A solid composition according to claim 1, wherein the hydrophilic polymer is PVA and the surfactant is selected from vitamin-E-polyethylene glycol-succinate (Vit-E-PEG-succinate), Polysorbate 20, Polysorbate 80, and sodium deoxycholate.

11. A process for preparing a solid composition according to claim 1, the process comprising:
   milling a solid form of lopinavir and ritonavir in the presence of
   at least one hydrophilic polymer selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof, and
   at least one surfactant selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof.

12. A method of treating a retroviral infection, the method comprising administering a therapeutically effective amount of a solid composition according to claim 1 to a patient suffering from or at risk of suffering from a retroviral infection.

13. A solid composition according to claim 1 for use in the treatment or delaying the appearance of clinical symptoms of a retrovirus infection wherein the solid composition is administered in combination with one or more other antiretroviral agents.

14. A pharmaceutical composition in a solid dosage form comprising a solid composition according to claim 1, and optionally one or more additional pharmaceutically acceptable excipients.

15. A pharmaceutical composition according to claim 14 for use in the treatment or delaying the appearance of clinical symptoms of a retrovirus infection wherein the pharmaceutical composition is administered in combination with one or more other antiretroviral agents.

16. A method of treating a retroviral infection, the method comprising administering a therapeutically effective amount of a pharmaceutical composition according to claim 14 to a patient suffering from or at risk of suffering from a retroviral infection.

17. A solid composition comprising:
   60-80% lopinavir and ritonavir combined;
   16-29 wt % PVA; and
   1-14 wt % vitamin-E-polyethylene glycol-succinate (Vit-E-PEG-succinate) or Polysorbate 80 as the surfactant.

* * * * *

UNITED STATES PATENT AND TRADEMARK OFFICE
CERTIFICATE OF CORRECTION

PATENT NO. : 9,532,979 B2  
APPLICATION NO. : 14/343453  
DATED : January 3, 2017  
INVENTOR(S) : Giardiello et al.

Page 1 of 1

It is certified that error appears in the above-identified patent and that said Letters Patent is hereby corrected as shown below:

In the Claims

In Column 30, Claim 2, Line 44, please delete "(m)." and insert -- (μm). -- therefor.

Signed and Sealed this  
Twenty-first Day of March, 2017

Michelle K. Lee  
*Director of the United States Patent and Trademark Office*